(12) United States Patent
Ozeki

(10) Patent No.: US 7,250,608 B2
(45) Date of Patent: Jul. 31, 2007

(54) RADIOGRAPHIC IMAGE DETECTOR AND RADIOGRAPHIC IMAGING SYSTEM

(75) Inventor: Hidekane Ozeki, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 218 days.

(21) Appl. No.: 11/155,407

(22) Filed: Jun. 17, 2005

(65) Prior Publication Data

US 2006/0202127 A1   Sep. 14, 2006

(30) Foreign Application Priority Data

Mar. 10, 2005   (JP)   ............... 2005-068111

(51) Int. Cl.
*G01T 1/24* (2006.01)
(52) U.S. Cl. ............... 250/370.08; 250/370.01; 250/370.09; 250/580; 250/581; 250/584; 378/89
(58) Field of Classification Search ........... 250/370.01, 250/370.08, 370.09
See application file for complete search history.

(56) References Cited

U.S. PATENT DOCUMENTS

| | | | | |
|---|---|---|---|---|
| 5,875,449 A * | 2/1999 | Ono | ............... | 711/100 |
| 6,216,225 B1 * | 4/2001 | Yoo | ............... | 713/2 |
| 6,389,105 B1 * | 5/2002 | Polichar et al. | ............ | 378/98.3 |
| 2003/0196008 A1 * | 10/2003 | Kim | ............... | 710/19 |
| 2005/0206769 A1 * | 9/2005 | Kump et al. | ........... | 348/333.01 |

FOREIGN PATENT DOCUMENTS

| | | |
|---|---|---|
| JP | 07-140255 A | 6/1995 |
| JP | 2000-206636 A | 7/2000 |
| JP | 2000-222061 A | 8/2000 |
| JP | 2003-172783 A | 6/2003 |
| JP | 2005-006979 A | 1/2005 |
| JP | 2005-102854 A | 4/2005 |

* cited by examiner

*Primary Examiner*—David Porta
*Assistant Examiner*—Casey Bryant
(74) *Attorney, Agent, or Firm*—Frishauf, Holtz, Goodman & Chick, P.C.

(57) ABSTRACT

A radiographic image detector to detect radiation applied thereto and obtain radiographic image information, includes: an internal power supply to supply power to drive units at least upon imaging; a communication unit to perform communication with an external device; a connection terminal connectable to a connection unit which performs at least one of charging of the internal power supply and the communication with the external device; a storing unit to store at least one of an image and information; a connection detecting unit to detect whether the connection terminal is connected to the connection unit; a state checking unit to check a state of each unit; and a control unit to control the state checking unit such that the state checking unit checks the state of each unit when the connection detecting unit has detected that the connection unit is connected to the connection terminal or disconnected therefrom.

13 Claims, 6 Drawing Sheets

RADIOGRAPHIC IMAGE DETECTOR AND RADIOGRAPHIC IMAGING SYSTEM

BACKGROUND OF THE INVENTION

1. Field of the Invention

The present invention relates to a radiographic image detector and a radiographic imaging system, and, in particular, to a radiographic image detector used without being connected to an external device at the time of imaging, and to a radiographic imaging system applying such a radiographic image detector.

2. Description of the Related Art

In the field of radiographic imaging for the purpose of medical diagnosis, there has been widely known a radiographic imaging system which irradiates a subject with radiation, detects an intensity distribution of the radiation having transmitted through the subject, and obtains a radiographic image of the subject. Moreover, in recent years, with respect to a radiographic imaging system, there has been developed and used a radiographic image detector called a "flat panel detector" (hereinafter, referred to as "FPD"), which is formed into a thin flat plate having a large number of photoelectric conversion elements arranged thereon in a matrix. The FPD detects the radiation having transmitted through the subject, photoelectrically converts the detected radiation into an electric signal, and performs image processing on the electric signal obtained after photoelectric conversion. It is thus possible to obtain easily and rapidly the radiographic image of the subject.

The radiographic image detector is broadly classified into a stationary detector installed as a part of the system at a predetermined position and a portable (cassette-type) detector freely portable. From a viewpoint of convenience in carriage and easy handling, utilization of the cassette-type radiographic image detector has been widely studied recently.

With respect to the cassette-type radiographic image detector, there has been known one which includes a rechargeable or replaceable internal power supply to drive the radiographic image detector, and is used without being connected to an external device such as an external power supply at the time of imaging. In case of using this kind of radiographic image detector to perform imaging without being connected to an external device, the radiographic image detector can be freely transported and installed depending on the site to perform imaging, and the like. This provides advantages that a degree of freedom in performing the imaging is improved and that it becomes easy to handle the radiographic image detector.

Meanwhile, with the radiographic image detector as described above, it is necessary to transfer radiographic image information acquired through imaging to the external device. Thus, there has been proposed, for example, a radiographic image detector which includes a memory for storing image information and transfers the image information stored in the memory to the external device through a connection terminal (for example, see JP-Tokukaihei-7-140255-A).

Further, in the radiographic image detector to perform imaging operation by using an internal power supply, when the amount of power remained in the internal power supply becomes small, it is necessary, for example, to connect the internal power supply to the external device in order to charge the internal power supply. Therefore, there has been proposed a radiographic image detector which is connected to the external device through a cradle and the like, to be able to charge the internal power supply and perform communication with the external device (for example, see JP-Tokukai-2000-206636-A). Further, there has been proposed a radiographic image detector capable of performing imaging and the like either in a state of being connected to the external device or disconnected therefrom (for example, see JP-Tokukai-2003-172783-A).

However, when imaging is performed without connecting the radiographic image detector to an external device such as the external power supply and with insufficient amount of power remained in the internal power supply, it is sometimes impossible to obtain a suitable image for correct diagnosis. Moreover, when imaging is erroneously performed while a memory to store image information, a communication unit to transmit the image information to the external device, and the like, are not functioning normally, the obtained image may not be stored or transferred to be wasted. In this case, re-imaging of the patient is required, and thus the patient is subjected to unnecessary exposure to radiation, which is unreasonable.

SUMMARY OF THE INVENTION

The present invention has been made to solve the above problems. An object of the invention is to provide a radiographic image detector and a radiographic imaging system, which prevent imaging from being performed when each unit is not in appropriate condition, thereby decreasing re-imaging and preventing the patient from being subjected to unnecessary exposure.

In order to achieve the above object, according to a first aspect of the present invention, a radiographic image detector to detect radiation applied thereto and obtain radiographic image information, comprises: an internal power supply to supply power to drive units at least at a time of imaging; a communication unit to perform communication with an external device; a connection terminal connectable to a connection unit which performs at least one of charging of the internal power supply and the communication with the external device; a storing unit to store at least one of an image and information; a connection detecting unit to detect whether the connection terminal is connected to the connection unit; a state checking unit to check a state of each unit; and a control unit to control the state checking unit such that the state checking unit checks the state of each unit when the connection detecting unit has detected that the connection unit is connected to the connection terminal or disconnected therefrom.

As described above, when the connection detecting unit has detected that the connection unit is connected to the connection terminal or disconnected therefrom, the state checking unit checks the state of each unit of the radiographic image detector. Accordingly, it is possible to prevent imaging from being performed when each unit is not in appropriate condition, thereby decreasing re-imaging and preventing the patient from being subjected to unnecessary exposure.

Preferably, the state checking unit includes at least any one of a remaining power detecting unit to perform a check for an amount of power remained in the internal power supply, a communication check unit to perform a communication check for the communication unit, and a memory check unit to perform a memory check for the storing unit.

As described above, the state checking unit includes at least any one of a remaining power detecting unit to perform a check for an amount of power remained in the internal power supply, a communication check unit to perform a communication check for the communication unit, and a memory check unit to perform a memory check for the storing unit. When the state check is performed through the remaining power detecting unit, even when the imaging is performed without the radiographic image detector being connected to an external device such as an external power supply, the imaging can be prevented from being erroneously performed with insufficient amount of power in the internal power supply. Moreover, when the state checks are performed through the communication check unit and the memory check unit, the imaging can be prevented from being erroneously performed while the memory to store the image information, the communication unit to transmit the image information to the external device, and the like, are not functioning normally. In this way, imaging failures owing to a shortage of the power and storage and transfer failures of the obtained image are prevented, thereby decreasing re-imaging and preventing the patient from being subjected to unnecessary exposure.

It is preferable that the communication unit includes a wired communication unit to perform wired communication with the external device and a wireless communication unit to perform wireless communication with the external device, and the communication check unit performs a communication check for at least one of the wired communication unit and the wireless communication unit.

As described above, the communication unit includes a wired communication unit to perform wired communication with the external device and a wireless communication unit to perform wireless communication with the external device. Accordingly, the communication unit can surely transmit and receive the image information, various control signals and the like to and from the external device. Here, the communication states of the wired communication unit and the wireless communication unit are checked by the communication check units. Accordingly, when transmission and reception of the various signals are not available, it is possible to prevent communication from being performed in vain and images from being not transferred. Thus, re-imaging is decreased and the patient is prevented from being subjected to unnecessary exposure.

Moreover, it is preferable that the connection terminal is any one of a charging connection terminal connectable to a charging connection unit to charge the internal power supply and a communication connection terminal connectable to a communication connection unit to perform communication with the external device, and the control unit controls the state checking unit to perform the state check for each unit in at least one of cases where the connection detecting unit has detected that the charging connection terminal is connected to or disconnected from the charging connection unit and where the connection detecting unit has detected that the communication connection terminal is connected to or disconnected from the communication connection unit.

When the connection terminal is any one of a charging connection terminal connectable to a charging connection unit and a communication connection terminal connectable to a communication connection unit, the state check is performed for each unit through the state check unit when the charging connection terminal or the communication connection terminal is connected to or disconnected from the corresponding connection unit. Accordingly, it is possible to perform a necessary state check for each of the cases where any one of the connection terminals is connected to the corresponding connection to start charging or communication operation, and where the any one of the connection terminals is disconnected from the corresponding connection unit to start imaging operation. Thus, it is prevented to perform imaging when any of the units is in an inappropriate condition, thereby decreasing re-imaging and preventing the patient from being subjected to unnecessary exposure.

Moreover, it is preferable that the connection terminal is a charging connection terminal connectable to a charging connection unit to charge the internal power supply, and the control unit controls the state checking unit to perform at least any one of the check for the amount of power remained in the internal power supply, the communication check for the communication unit and the memory check for the storing unit when the connection detecting unit has detected that the charging connection terminal is disconnected from the charging connection unit, and controls the state checking unit to perform the communication check for the communication unit when the connection detecting unit has detected that the charging connection terminal is connected to the charging connection unit.

As described above, when the connection terminal is a charging connection terminal connectable to a charging connection unit, and when the charging connection terminal is disconnected from the charging connection unit, the check for the amount of power remained in the internal power supply, communication check for the communication unit and memory check for the storing unit can be performed prior to imaging operation. Thus, it is prevented to perform imaging when any of the units is in an inappropriate condition, thereby decreasing re-imaging and preventing the patient from being subjected to unnecessary exposure. Moreover, when the charging connection terminal is connected to the charging connection unit, the communication check for the communication unit is performed. Thus, for example, it is possible to prevent such as failures in image information transfer after imaging, thereby decreasing re-imaging and preventing the patient from being subjected to unnecessary exposure.

Moreover, it is preferable that the connection terminal is a communication connection terminal connectable to a communication connection unit to perform communication with the external device, and the control unit controls the state checking unit to perform at least any one of the communication check for the wireless communication unit, the check for the amount of power remained in the internal power supply, and the memory check for the storing unit when the connection detecting unit has detected that the communication connection terminal is disconnected from the communication connection unit, and controls the state checking unit to perform the communication check for the communication unit when the connection detecting unit has detected that the communication connection terminal is connected to the communication connection unit.

As described above, when the connection terminal is a communication connection terminal connectable to a communication connection unit, and when the communication connection terminal is disconnected from the communication connection unit, it is possible to perform the communication check for the wireless communication unit, check for the amount of power remained in the internal power supply, and memory check for the storing unit. Thus, it is prevented to perform imaging when any of the units is in an inappropriate condition, thereby decreasing re-imaging and preventing the patient from being subjected to unnecessary exposure. Moreover, when the communication connection terminal is connected to the communication connection unit, the communication check for the communication unit is performed. Thus, it is possible to prevent such as failures in image information transfer, thereby decreasing re-imaging and preventing the patient from being subjected to unnecessary exposure.

Further, it is preferable that the radiographic image detector further comprises a notifying unit to notify that the state checking unit has detected that a state of each unit is not normal.

When imaging and the like are erroneously performed with any of the units is in an inappropriate condition, accurate radiographic image information cannot be obtained. Accordingly, it is necessary to perform re-imaging, and the patient is subjected to unnecessary exposure. According to the invention, when any of the units is in an inappropriate condition, the operator is notified of the above state. Therefore, it is possible to prevent that imaging is performed under a condition inappropriate for imaging, thereby avoiding unnecessary exposure.

Moreover, it is preferable that the radiographic image detector is a cassette-type flat panel detector to detect radiation applied thereto, convert the radiation into an electric signal, store the electric signal, and read the stored electric signal, to acquire the radiographic image information.

As described above, the radiographic image detector is the cassette-type FPD, and is easily transported to any imaging site, and thus a degree of freedom in imaging is improved. It is convenient to use such a radiographic image detector without being connected to an external device such as an external power supply at the time of imaging. According to the invention, the state of each unit is checked by detecting whether the detector is connected to or disconnected from an external device. Thus, it is possible to prevent that imaging is performed under a condition inappropriate for imaging, thereby avoiding unnecessary exposure.

According to a second aspect of the present invention, a radiographic imaging system comprises: the radiographic image detector; and a console to operate the radiographic image detector.

Thus, imaging is performed by using the radiographic image detector in which, when the connection detecting unit has detected that the connection terminal is connected to or disconnected from the connection unit, the state checking unit checks the state of each unit. Thus, it is possible to prevent imaging from being performed when any of the units is in an inappropriate condition, thereby decreasing re-imaging and preventing the patient from being subjected to unnecessary exposure.

Moreover, it is preferable that the console in the radiographic imaging system comprises: a communication unit to perform communication with the radiographic image detector; and a notifying unit to notify that the communication unit has received a signal indicating that the state checking unit of the radiographic image detector has detected that each unit is not normal.

Thus, in the console, it is possible to grasp information as to whether each unit of the radiographic image detector is in a state capable of operating normally, when the communication unit of the console has received the signal from the radiographic image detector. Therefore, the operator can manage the radiographic image detector entirely by the console, which is convenient. Meanwhile, when a signal indicating that any of the units of the radiographic image detector is not in the normal state, the information is displayed on a display unit of the console. Accordingly, the operator can easily check through the console whether the respective units of the radiographic image detector are in the state capable of operating normally, and thus it is possible to surely prevent unnecessary exposure due to re-imaging.

DETAILED DESCRIPTION OF THE PREFERRED EMBODIMENT

An embodiment of the present invention will be described below with reference to FIGS. 1 to 6.

Figure 1:
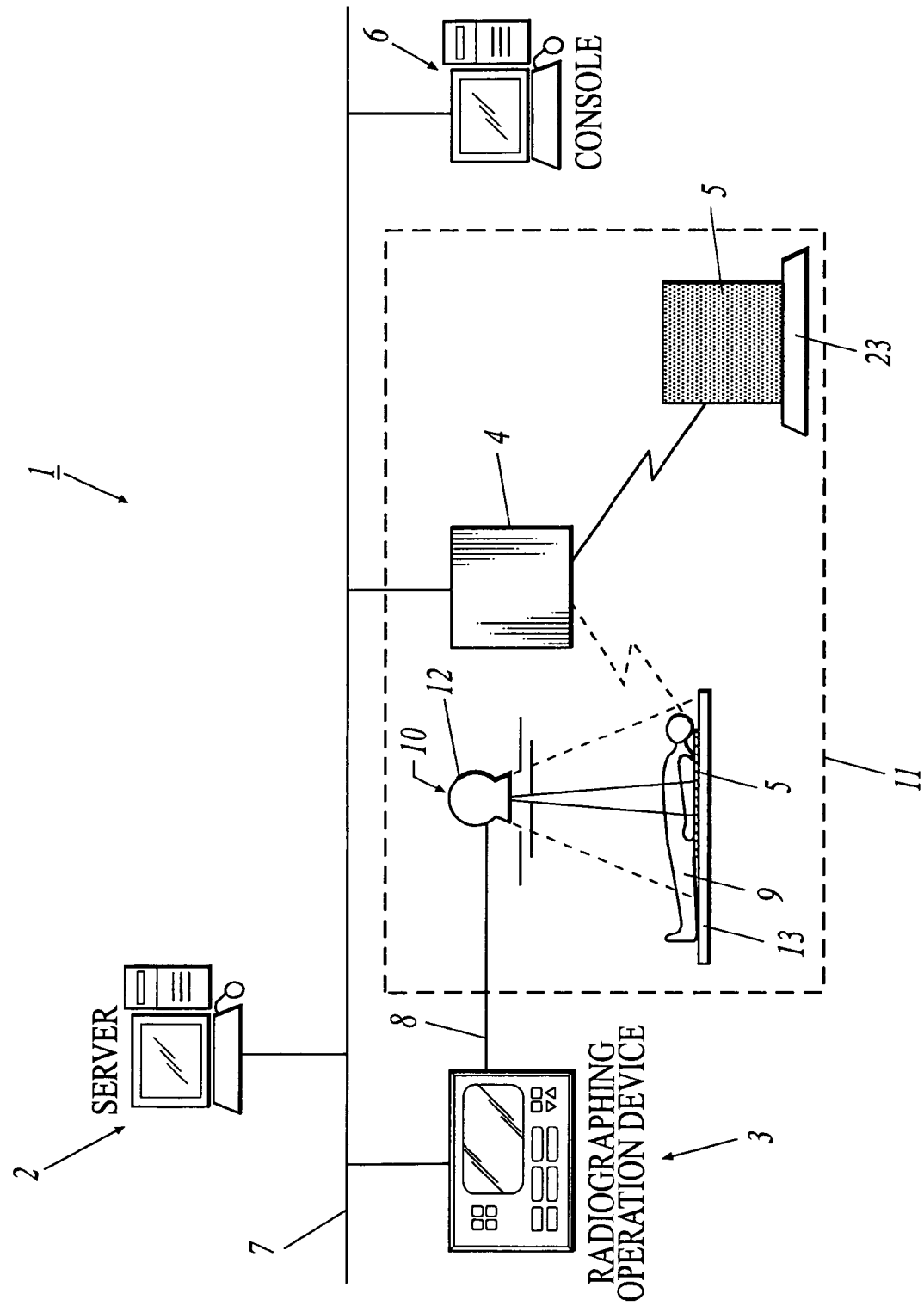
FIG. 1 is a view showing a schematic configuration illustrating an embodiment of a radiographic imaging system according to the present invention.

FIG. 1 is a view showing a schematic configuration of an embodiment of a radiographic imaging system applying a radiographic image detector of the invention.

A radiographic imaging system 1 of the embodiment is, for example, a system applied to radiographic imaging performed in a hospital. As shown in FIG. 1, connected through a network 7 are: a server 2 to manage various kinds of information concerning the radiographing and a patient, and the like; a radiographing operation device 3 to perform an operation regarding the radiographic imaging; a base station 4 to perform communication by a wireless communication system such as a wireless LAN (local area network); and a console 6 to perform such as operation of a radiographic image detector 5 and image processing on a radiographic image detected by the radiographic image detector 5. A radiographic imaging device 10 to irradiate the patient as a subject 9 with radiation to perform radiographic imaging is connected to the radiographing operation device 3 through a cable 8. The radiographic imaging device 10 and radiographic image detector 5 are, for example, installed in one imaging room 11, and radiographic image information can be obtained by operating the radiographic imaging device 10 with the radiographing operation device 3 and detecting the radiographic image with the radiographic image detector 5. Alternatively, a plurality of radiographic image detectors 5 may be provided in one imaging room 11.

The network 7 may be a communication line dedicated to the system; however, the network 7 is preferably an existing line such as Ethernet (registered trademark), since otherwise the degree of freedom in system configuration would be decreased, or for other reasons. In addition to the above devices, to the network 7, there may be connected a plurality of radiographing operation devices 3 to operate radiographic imaging devices 10 placed in other imaging rooms 11, radiographic image detectors 5, and consoles 6.

The radiographing operation device 3 includes: an input operation unit to operate the radiographic imaging device 10 by, for example, inputting a signal for a radiographing condition or the like, the input operation unit including an operation panel and the like; a display unit to display information on the radiographing condition etc., various instructions, and the like; a power supply unit to supply power to the radiographic imaging device 10; and the like (none of them are shown).

The radiographic imaging device 10 is placed inside the imaging room 11. The radiographic imaging device 10 includes a radiation source 12, and radiation is generated by applying a tube voltage to the radiation source 12. For the radiation source 12, for example, a radiation tube is used. The radiation tube generates radiation by accelerating under a high voltage electrons generated by thermal excitation and allowing the electrons to collide with a cathode.

The radiographic image detector 5 detects radiation which has been emitted from the radiation source 12 of the radiographic imaging device 10 and has transmitted through the subject 9, to acquire a radiographic image. The radiographic image detector 5 is disposed to be within the coverage of the radiation emitted from the radiation source 12 at the time of radiographing. The radiographic image detector 5 is disposed, for example, as shown in FIG. 1, between the subject 9 and a bed 13 on which the subject 9 lies down. However, the position thereof is not limited thereto. For example, there may be provided below the bed a detector placing opening (not shown) through which the radiographic image detector 5 is to be placed, and the radiographic image detector 5 may be inserted into the detector placing opening.

The radiographic image detector 5 is of a flat-panel type. A structure of the radiographic image detector 5 will be described below with reference to FIGS. 2 to 5.

Figure 2:
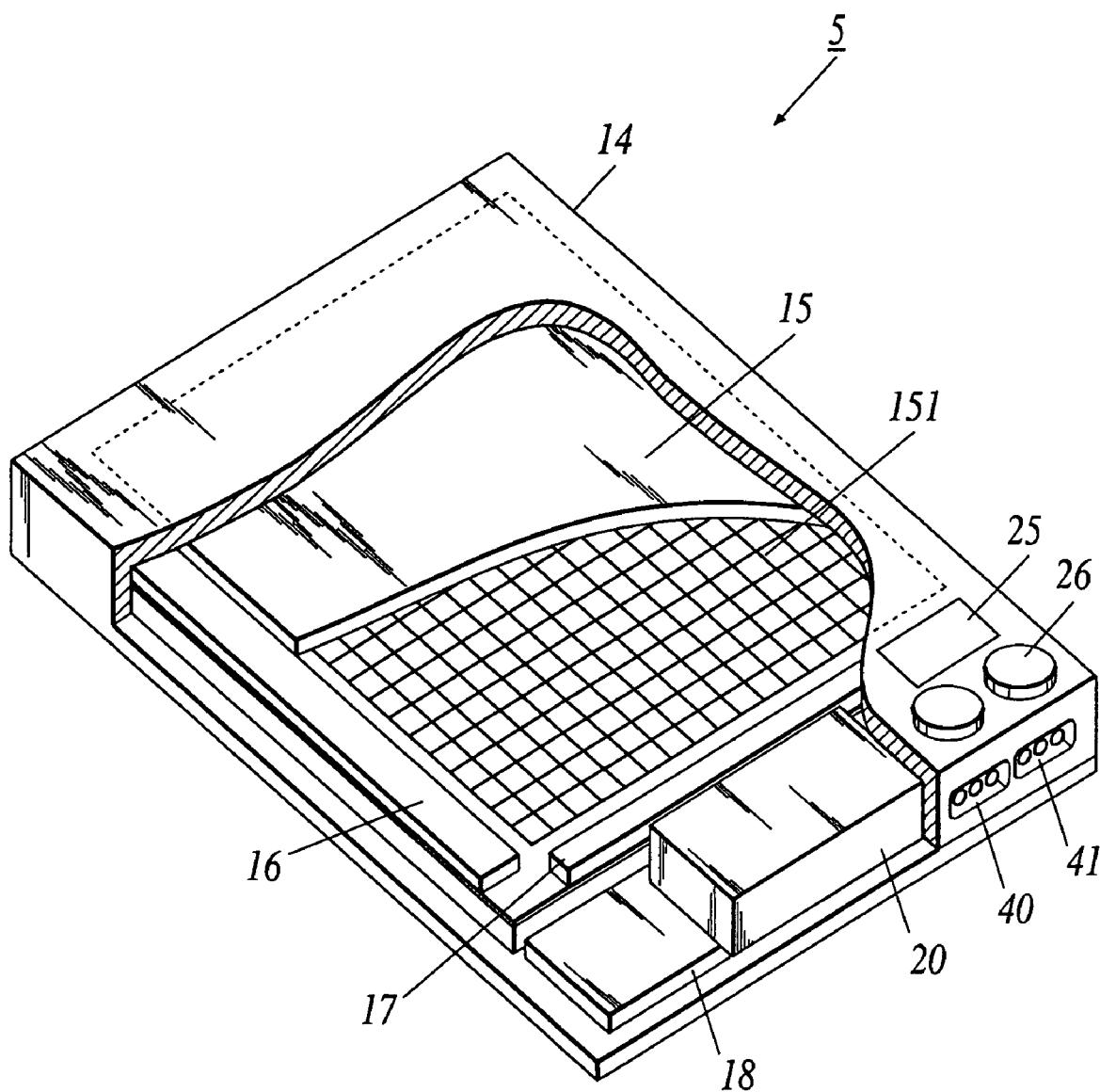
FIG. 2 is a perspective view showing a structure of main part of a radiographic image detector according to the present invention.

As shown in FIG. 2, the radiographic image detector 5 includes a casing 14 to protect inside the detector, and is configured to be a cassette to be portable.

Inside the casing 14, formed is a layered imaging panel 15 to convert emitted radiation into an electric signal. On a surface-to-be-irradiated of the imaging panel 15, provided is a light-emitting layer (not shown) to emit light in accordance with intensity of the radiation which is made incident thereonto.

The light-emitting layer is one generally called a scintillator layer, and, for example, contains phosphor as a main component and outputs an electromagnetic wave with a wavelength of 300 to 800 nm, that is, an electromagnetic wave (light) of not only visible light but light ranging from ultraviolet light to infrared light.

For the phosphor to be used in the light-emitting layer, for example, phosphor containing $CaWO_4$ or the like as a basic substance and phosphor formed by actively imparting a main light-emitting substance into a basic substance such as CsI:Tl, $Gd_2O_2S$:Tb, and ZnS:Ag may be used. Moreover, phosphor represented by a general formula $(Gd, M, Eu)_2O_3$ where M is a rare-earth element can be used. In particular, CsI:Tl and $Gd_2O_2S$:Tb are preferable because of high radiation absorption and light-emitting efficiencies thereof. By using these substances, a low-noise and high-quality image can be obtained.

On the surface opposite to the surface-to-be-irradiated of the light-emitting layer, formed is a signal detection unit 151 which converts electromagnetic wave (light) outputted from the light-emitting layer into electric energy and stores the electric energy. The signal detection unit 151 further outputs an image signal based on the stored electric energy.

Figure 3:
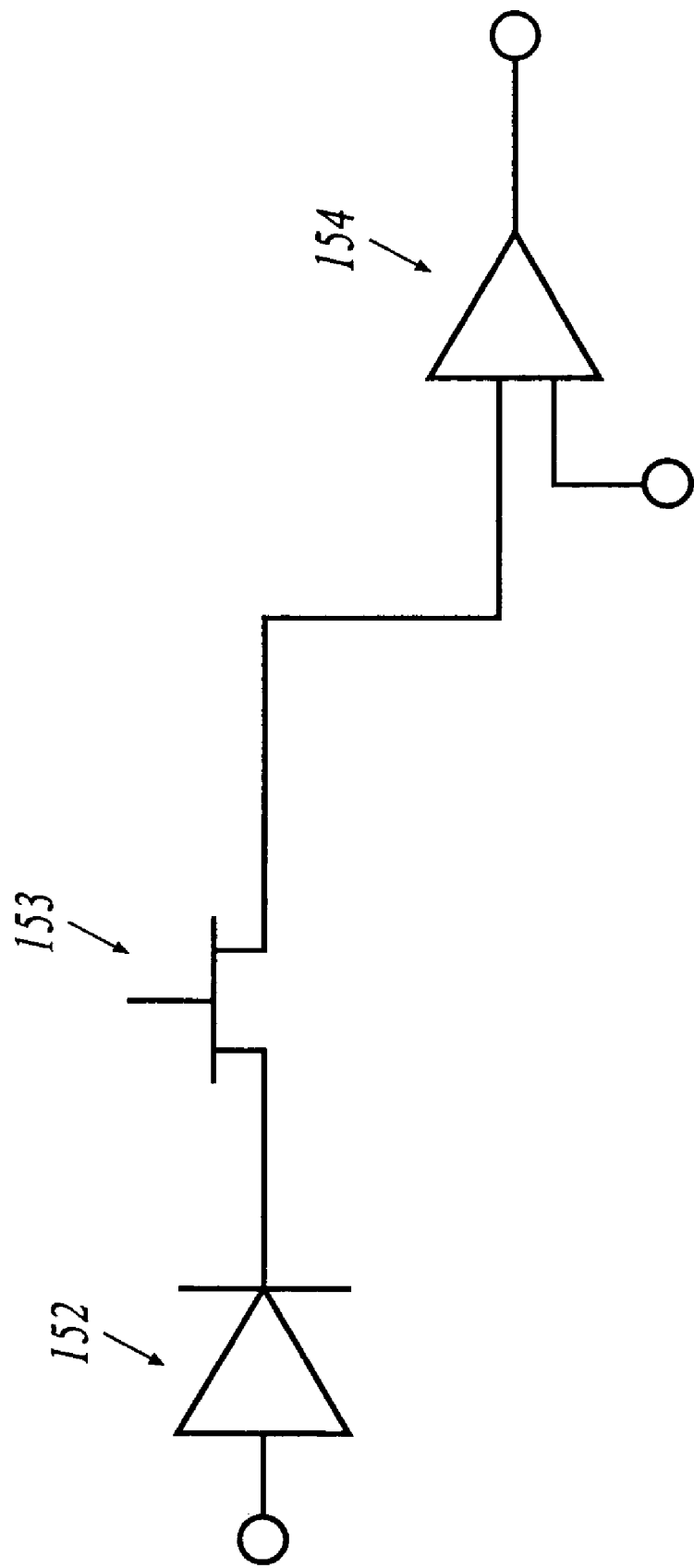
FIG. 3 is a configuration view of an equivalent circuit for one pixel in a photoelectric conversion unit constituting a signal detection unit.

A circuit configuration of the imaging panel 15 will now be described. FIG. 3 is an equivalent circuit diagram of a photoelectric conversion unit for one pixel constituting the signal detection unit 151.

As shown in FIG. 3, the photoelectric conversion unit for one pixel includes a photodiode 152, and a thin-film transistor (hereinafter referred to as "TFT") 153 to extract electric energy stored in the photodiode 152 as an electric signal by switching. The extracted electric signal is amplified by an amplifier 154 to such a level that a signal reading circuit 17 can detect the amplified electric signal. To the amplifier 154, a reset circuit (not shown) including a TFT 153 and a capacitor is connected. The reset circuit performs a reset operation for resetting the stored electric signal by switching on the TFT 153. The photodiode 152 may be a photodiode simply having a parasitic capacitance, or may include additional capacitors in parallel in order to improve dynamic ranges of the photodiode 152 and the photoelectric conversion unit.

Figure 4:
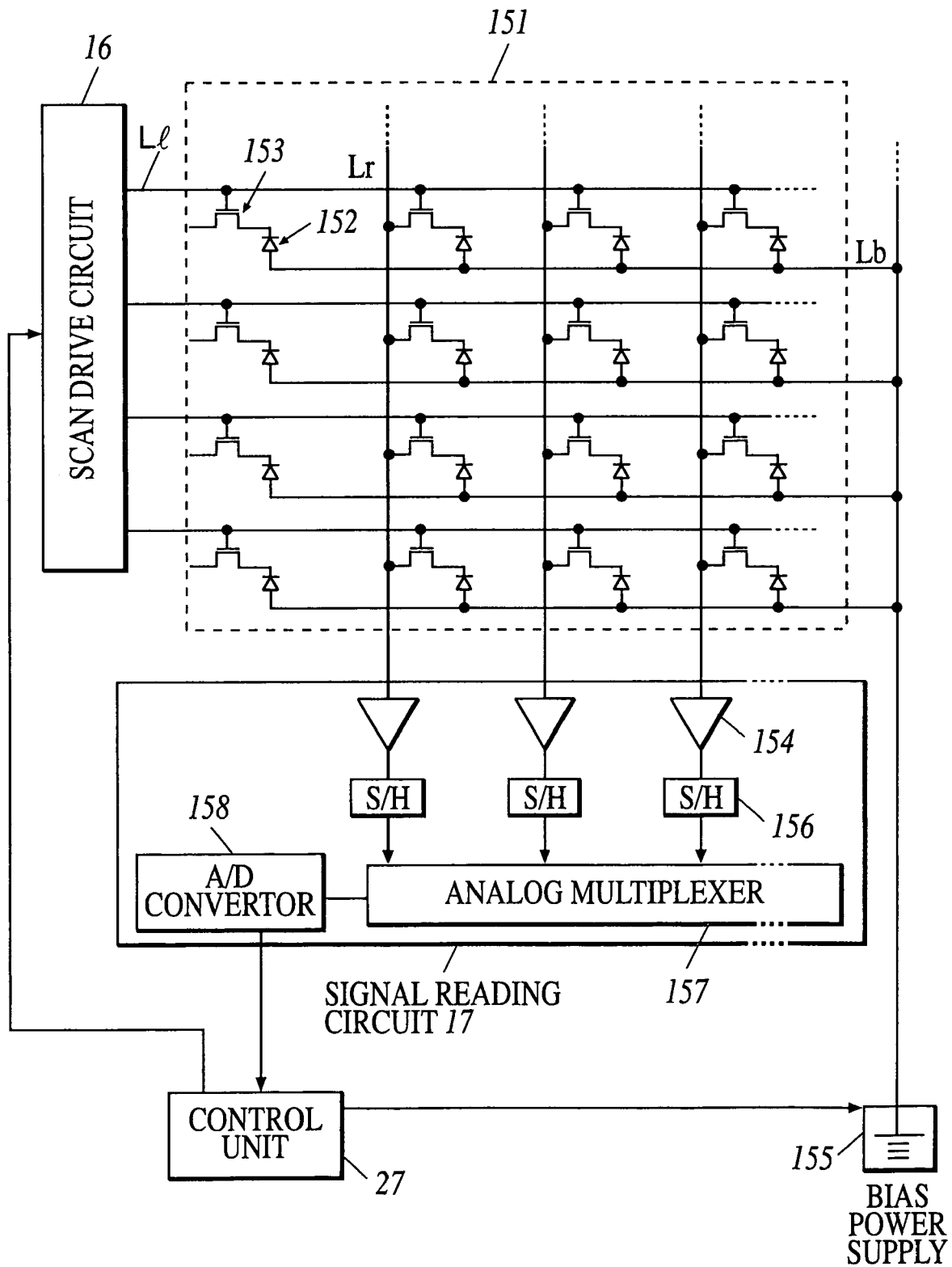
FIG. 4 is a configuration view of an equivalent circuit in which the photoelectric conversion units shown in FIG. 2 are arranged two-dimensionally.

FIG. 4 is an equivalent circuit diagram in which the above-described photoelectric conversion units are arranged two-dimensionally. Between the pixels, scan lines Ll and signal lines Lr are arranged to be perpendicular to each other. A TFT 153 is connected to each photodiode 152, and one end of the photodiode 152 on a side to which the TFT 153 is connected is connected to the signal line Lr. The other end of the photodiode 152 is connected to one end of the adjacent photodiode 152 in the same row, and connected to a bias power supply 155 through a common bias line Lb. One end of the bias power supply 155 is connected to a control unit 27, and thus a voltage is applied to the photodiodes 152 through the bias line Lb according to an instruction from the control unit 27. The TFTs 153 arranged in the same row are connected to their common scan line Ll, and each scan line Ll is connected to the control unit 27 through a scan drive circuit 16. Similarly, the photodiodes 152 arranged in the same row are connected to their common signal line Lr, and connected to the signal reading circuit 17 controlled by the control unit 27. In the signal reading circuit 17, an amplifier 154, a sample/hold circuit 156, an analog multiplexer 157 and an A/D converter 158 are arranged on the same signal line Lr in this order when viewed from the imaging panel 15.

The TFT 153 may be of an inorganic semiconductor series or one using an organic semiconductor, which are used in a liquid crystal display and the like.

Moreover, although the photodiodes 152 are used as the photoelectric conversion elements in this embodiment, solid-state imaging elements other than the photodiodes 152 may be used as the photoelectric conversion elements.

As shown in FIG. 2, on side portions of the signal detection unit 151, disposed are the scan drive circuit 16 to scan and drive the respective photoelectric conversion elements by sending pulses to the photoelectric conversion elements, and the signal reading circuit 17 to read the electric energy stored in the respective photoelectric conversion elements.

The radiographic image detector 5 includes, as storing means, an image storing unit 18 which is, for example, a rewritable memory such as a RAM (random access memory) or a flash memory. The image storing unit 18 stores an image signal outputted from the imaging panel 15. The image storing unit 18 may be a built-in memory or a detachable memory such as a memory card.

Moreover, an internal power supply 20 to supply power to a plurality of drive units (for example, the scan drive circuit 16, the signal reading circuit 17, a communication unit (described later), the image storing unit 18, state checking means (described later), an indicator 25 (described later), an input operation unit 26 (described later), the imaging panel 15, and the like) constituting the radiographic image detector 5 is provided in the radiographic image detector 5.

The internal power supply 20 may be any one of various batteries including, for example, a manganese battery, an alkaline battery, an alkaline button battery, a lithium battery, a silver oxide battery, an air-zinc battery, a nickel-cadmium battery, a mercury battery and a lead battery, or a rechargeable battery such as a nickel-cadmium battery, a nickel-hydrogen battery, a lithium-ion battery, a small sealed lead battery, a lead-acid battery, a fuel battery, and a solar battery. In this embodiment, a case of using a rechargeable battery as the internal power supply 20 will be described.

The shape of the internal power supply 20 is not limited to that illustrated in FIG. 2. For example, the internal power supply 20 formed in a plate shape may be provided in parallel to the imaging panel 15. By forming the internal power supply 20 into such a shape, the area of the imaging panel 15 can be increased and thus an imaging-enabled area can be widened.

On one end of the casing 14, there are provided a connection terminal 40 for charging, which is connected to connection means for charging the internal power supply 20, and a connection terminal 41 for communication, which is connected to connection means for allowing communication with an external device such as the console 6. In this embodiment, a cradle 23 functions as the connection means for charging and the connection means for communication. On the cradle 23, connection terminals (not shown) connected to the connection terminal 40 for charging and to the connection terminal 41 for communication on the radiographic image detector 5 are provided individually.

For example, as shown in FIG. 1, the radiographic image detector 5 is attached onto the cradle 23, and thus the connection terminal 40 for charging of the casing 14 and the connection terminal of the cradle 23 are connected to each other. Power is thus supplied from the cradle 23 or from an external power supply (not shown) connected to the cradle 23, and the internal power supply 20 is charged.

Moreover, in the radiographic image detector 5, there is provided a wired communication unit 21 (refer to FIG. 5) to transmit and receive various signals by wire to and from an external device such as the console 6. For example, the radiographic image detector 5 is attached onto the cradle 23, and the connection terminal 41 for communication of the casing 14 and the connection terminal of the cradle 23 are connected to each other. The wired communication unit 21 is thus connected to the external device such as the console 6 through the above-described connection terminal 41 for communication. In this way, for example, an image signal outputted from the imaging panel 15 is transferred to the console 6 or the like, and an imaging start signal or the like transmitted from the console 6 or the like is received.

Further, in the radiographic image detector 5, there is provided a wireless communication unit 22 (refer to FIG. 5) to perform wireless communication, which transmits and receives various signals wirelessly to and from an external device such as the console 6. The wireless communication includes, for example, optical communication using light such as an infrared ray, visible light and an ultraviolet ray, communication using a radio wave, and the like. However, the wireless communication is not limited thereto.

Moreover, on one end on a surface of the casing 14, the indicator 25 to display the amount of power remained in the internal power supply 20, states of the respective units constituting the radiographic image detector 5, various operation statuses and the like is provided. An operator can visually confirm the states of the respective units and the like through the indicator 25. Particularly in this embodiment, the indicator 25 displays the amount of power remained in the internal power supply 20, communication states of the wired communication unit 21 and the wireless communication unit 22, the amount of memory available in the image storing unit, and the like. When the state of the unit(s) are not normal, the indicator 25 functions as notifying means for notifying the operator of the abnormal state(s).

On the outer side of the casing 14, provided is the input operation unit 26 through which the operator such as a radiologist inputs and sets the imaging condition, identification information on the patient, various instructions, and the like. Note that contents which can be inputted from the input operation unit 26 are not limited to those illustrated here.

Figure 5:
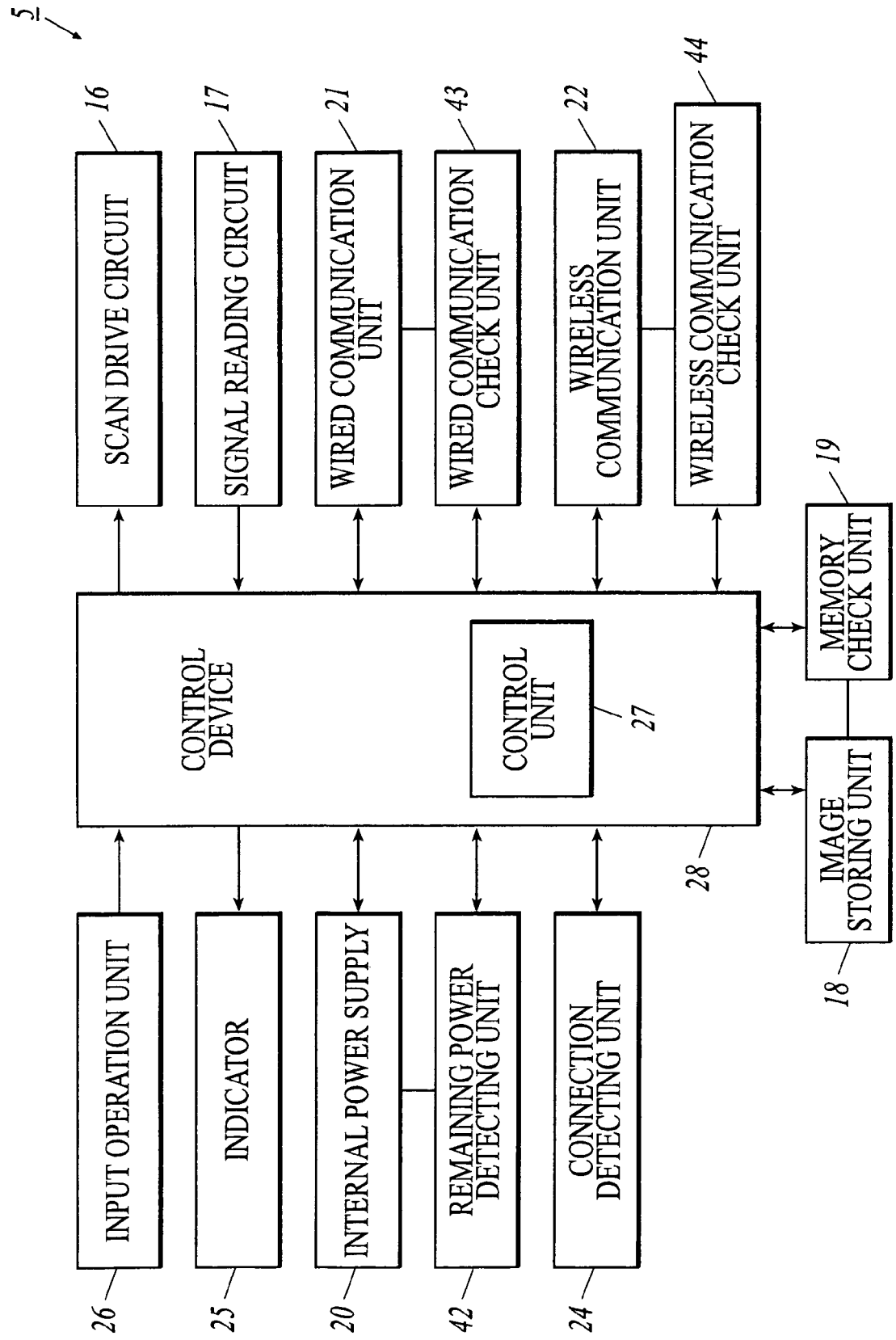
FIG. 5 is a block diagram showing a configuration of main part of the radiographic image detector according to the present invention.

Moreover, as shown in FIG. 5, the radiographic image detector 5 comprises a control device 28 provided with the control unit 27 including, for example, a general-purpose CPU, ROM, RAM and the like (none of them are shown). The control unit 27 reads predetermined programs stored in the ROM to develop the programs in a work area of the RAM, and allows the CPU to execute various kinds of processing according to the programs.

Besides the programs, various control data is stored in the ROM. Particularly in this embodiment, stored as the control data is, for example, remaining amount determination data for determining whether the amount of power remained in the internal power supply 20 is a predetermined amount or more that is enough amount to perform imaging, determination data for determining whether the respective drive units such as the wired communication unit 21, wireless communication unit 22 and image storing unit 18 can operate normally, and the like.

Moreover, the radiographic image detector 5 includes state checking means for checking whether the respective units are in states capable of performing normal imaging. In this embodiment, a check for the amount of power remained in the internal power supply 20, checks for communication in the wired communication unit 21 and the wireless communication unit 22, and a check for the memory of the image storing unit 18 are performed as the state checks. The state checking means is provided for each of state checks. Each of the state checking means will now be described.

The radiographic image detector 5 includes a remaining power detecting unit 42 as state checking means for checking the remaining amount of power. The remaining power detecting unit 42 performs a remaining amount detection to detect the amount of power remained in the internal power supply 20 based on the control by the control unit 27, checks whether the obtained amount of power remained in the internal power supply 20 is the predetermined amount or more to be enough to allow imaging, and outputs the obtained result to the control unit 27.

Moreover, the radiographic image detector 5 includes a wired communication check unit 43 and a wireless communication check unit 44 as checking means for checking the communication state. The wired communication check unit 43 and the wireless communication check unit 44 detect, for example, intensity of a transmitted/received signal, a time required for the transmission/reception, and the like, and check whether the wired communication unit 21 and the wireless communication unit 22 can exchange normally the signal with an external device such as the console 6 and the server 2, or transfer normally an image based on the control of the control unit 27. The wired communication check unit 43 and the wireless communication check unit 44 output a result obtained by the check to the control unit 27.

Moreover, the radiographic image detector 5 includes a memory check unit 19 as means for checking the state of the memory. The memory check unit 19 checks whether the image storing unit 18 can store normally the image information based on the control of the control unit 27 and whether a sufficient memory capacity for storing the image information is remained, and outputs the obtained result to the control unit 27.

Moreover, the radiographic image detector 5 includes a connection detecting unit 24 to detect whether the above-described connection terminal 40 for charging and connection terminal 41 for communication are connected to the cradle 23 which is connection means. The connection detecting unit 24 is, for example, a contact sensor (not shown) or the like disposed in the vicinity of the connection terminal 40 for charging and the connection terminal 41 for communication. The connection detecting unit 24 detects that the connection terminal 40 for charging and the connection terminal 41 for communication are brought into contact with the connection terminal of the cradle 23. The unit to detect whether the connection terminal 40 for charging and the connection terminal 41 for communication are connected to the cradle 23 is not limited to the above. For example, whether or not the connection terminal 40 for charging and the connection terminal 41 for communication are connected to the cradle 23 may be detected by detecting such as whether power is supplied to the connection terminal 40 for charging from the external device. The connection detecting unit 24 outputs the detection result to the control unit 27, and, based on the detection result sent from the connection sensing means 24, the control unit 27 recognizes whether the connection terminal 40 for charging and the connection terminal 41 for communication are connected to the cradle 23.

In this embodiment, when the connection detecting unit 24 has detected that the connection terminal 40 for charging and the connection terminal 41 for communication are connected to the cradle 23 or that the connection is released, the control unit 27 controls the respective state checking means to perform the state checks.

Specifically, when the connection detecting unit 24 has detected that the connection terminal 40 for charging and the connection terminal of the cradle 23 are connected to each other, the control unit 27 allows the wireless communication check unit 44 to operate, thus performing the state check as to whether or not the wireless communication unit 22 is in a state capable of transmitting and receiving the information normally. In this case, the wired communication unit 21 transmits the result of the state check performed for the wireless communication unit 22, and thus the control unit 27 can acquire the result of the state check even when the wireless communication unit 22 is in a state incapable of transmitting and receiving the information normally. Then, the control unit 27 compares the result of the state check with the determination data in the ROM, and determines whether or not the wireless communication unit 22 can transmit and receive the information normally. When it is determined as a result of the determination that the wireless communication unit 22 can make communication normally, the control unit 27 may control the wireless communication unit 22 to transmit the image information to an external device such as the console 6.

Moreover, when the connection detecting unit 24 has detected that the connection terminal 41 for communication and the connection terminal of the cradle 23 are connected to each other, the control unit 27 allows the wired communication check unit 43 to operate, thus performing the state check as to whether or not the wired communication unit 21 can transmit and receive the information normally. The control unit 27 compares the result of the state check with the determination data in the ROM, and determines whether the wired communication unit 21 can transmit and receive the information normally. When it is determined as a result of the determination that the wired communication unit 21 can make communication normally, the control unit 27 may control the wired communication unit 21 to transmit the image information to an external device such as the console 6. Moreover, when the wired communication unit 21 is normal, the control unit 27 may further allow the wireless communication check unit 44 to operate, and may perform the state check as to whether or not the wireless communication unit 22 is in a state capable of transmitting and receiving the information normally. In this case, the wired communication unit 21 is allowed to transmit the result of the state check for the wireless communication unit 22, and thus the control unit 27 can acquire the result of the state check even when the wireless communication unit 22 is in a state incapable of transmitting and receiving the information normally. Then, it is determined as the result of the state check that the wireless communication unit 22 can transmit and receive the information normally, and the control unit 27 may control the wireless communication unit 22 to transmit the image information to an external device such as the console 6.

In contrast, when the connection detecting unit 24 has detected that the connection between the connection terminal 40 for charging and the connection terminal of the cradle 23 is released, the control unit 27 controls the respective state checking means to perform the state checks as to whether or not the respective units are in a state capable of performing the imaging operation normally. There is a high possibility that the radiographic image detector 5 is used for imaging immediately after being detached from the cradle 23. Accordingly, the states of the respective units are checked prior to the imaging operation, thus avoiding performing imaging in vain. Specifically, the control unit 27 controls the remaining power detecting unit 42 to perform the state check as to whether the amount of power remained in the internal power supply 20 is the predetermined amount or more to be enough to allow imaging. Moreover, the control unit 27 controls the memory check unit to perform the state checks as to whether the image storing unit 18 can store the image information normally and whether memory capacity sufficient for storing the image information is remained. Furthermore, the control unit 27 controls the wired communication check unit 43 and the wireless communication check unit 44 to check whether the wired communication unit 21 and the wireless communication unit 22 can exchange normally the signal with an external device such as the console 6 and the server 6, or whether the wired communication unit 21 and the wireless communication unit 22 can transfer the image normally. The control unit 27 compares results of the state checks described above with the determination data in the ROM, and determines whether the states of the respective units are normal.

When the connection detecting unit 24 has detected that the connection between the connection terminal 41 for communication and the connection terminal of the cradle 23 is released, the control unit 27 controls the remaining power detecting unit 42 to perform the state check as to whether the amount of power remained in the internal power supply 20 is the predetermined amount or more to be enough to allow imaging. Moreover, the control unit 27 controls the memory check unit to perform the state checks as to whether the image storing unit 18 can store the image information normally, and whether memory capacity sufficient for storing the image information is remained. Further, the control unit 27 controls the wireless communication check unit 44 to check whether the wireless communication unit 22 can exchange normally the signal with an external device such as the console 6 and the server 2, or whether the wireless communication unit 22 can transfer the image normally. The control unit 27 compares results of the state checks as described above with the determination data in the ROM, and determines whether the states of the respective units are normal.

Moreover, the control unit 27 allows the indicator 25 to display the results of the state checks by the respective state checking means. Specifically, when the amount of power remained in the internal power supply 20 is the predetermined amount or more to be enough to allow imaging, and when both results of the communication check and memory check are normal, the control unit 27 controls the indicator 25 to display that imaging is possible. When the amount of power remained in the internal power supply 20 is the predetermined amount or more, and when either the result of the communication check or the result of the memory check is not normal, the control unit 27 controls the indicator 25 to display that at least any one of the wired communication unit 21, wireless communication unit 22 and image storing unit 18 is in a state incapable of performing the operation normally. Further, when the amount of power remained in the internal power supply 20 is less than the predetermined amount while the results of the communication check and memory check are normal, the control unit 27 controls the indicator 25 to display that the amount of power remained in the internal power supply 20 is less than the predetermined amount necessary for imaging. Note that contents to be displayed on the indicator 25 are not limited to the above, and, for example, display may be performed only when some abnormality is found as the results of the state checks.

Further, when the result of the communication check is normal, the control unit 27 causes the console 6 to transmit the result as the state information on the respective units of the radiographic image detector 5, through either the wired communication unit 21 or the wireless communication unit 22 as appropriate. The state information on the respective units, which has been obtained as the result of the state check, may always be transmitted to the console 6, or may be transmitted to the console 6 only when some abnormality is found.

In this embodiment, by attaching and detaching the radiographic image detector 5 to and from the cradle 23, both of the connection terminal 40 for charging and the connection terminal 41 for communication are connected to and disconnected from the connection terminals of the cradle 23.

The information inputted from the input operation unit 26 and the signal received from the communication unit are sent to the control unit 27, and the control unit 27 controls the respective drive units based on the signals sent from the control unit 27.

The control unit 27 drives the scan drive circuit 16 to send the pulses to the respective photoelectric conversion elements, thus scanning and driving the respective photoelectric conversion elements. Then, the image signal is read by the signal reading circuit 17 which reads the electric energy stored in the respective photoelectric conversion elements, and the image signal thus read is sent to the control unit 27.

The control unit 27 allows the image storing unit 18 to store the image signal. The image signal stored in the image storing unit 18 is sent through the communication unit to the console 6 as appropriate.

Figure 6:
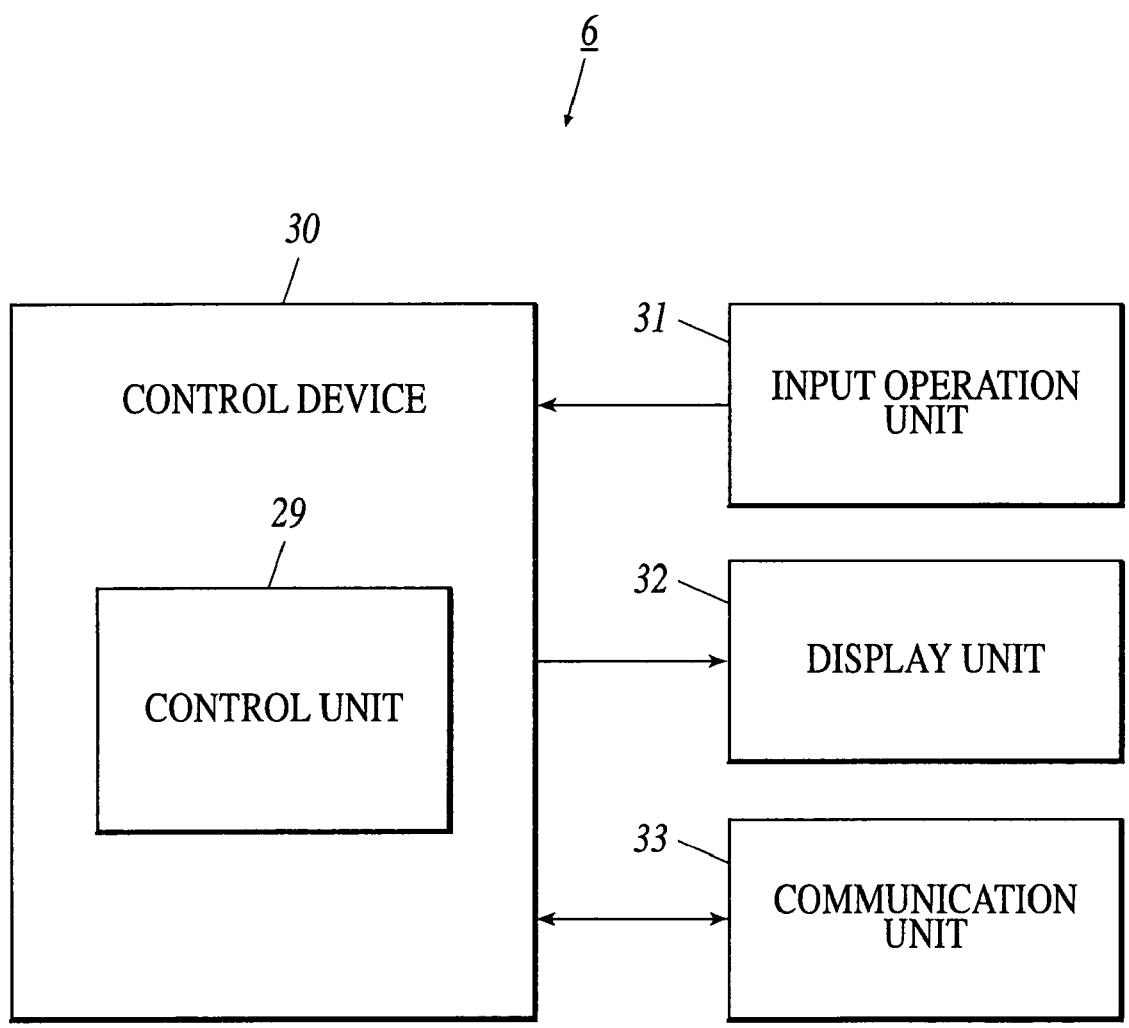
FIG. 6 is a block diagram showing a configuration of main part of a console constituting the radiographic imaging system of FIG. 1.

As shown in FIG. 6, the console comprises a control device 30 including a control unit 29 which includes, for example, a general-purpose CPU, ROM, RAM and the like (none of them are shown). The control unit 29 reads predetermined programs stored in the ROM to develop the programs in a work area of the RAM, and allows the CPU to execute various kinds of processing according to the programs.

Moreover, the console 6 includes an input operation unit 31 to input various types of instructions and the like, a display unit 32 to display an image, various messages and the like, a communication unit 33 as communication means for transmitting and receiving a signal to and from an external device such as the radiographic image detector 5, and the like.

The input operation unit 31 includes, for example, an operation panel, a keyboard, a mouse and the like, and outputs as input signals a press signal sent from a key pressed on the operation panel or keyboard and an operation signal sent from the mouse, to the control unit 29.

The display unit 32 includes, for example, a CRT (cathode ray tube), an LCD (liquid crystal display) and the like, and displays various contents according to an instruction of a display signal outputted from the control unit 29.

In this embodiment, when it is determined that the respective units of the radiographic image detector 5 are not in a state capable of operating normally based on the check results of the respective checking means described above, and when the determination result is sent as a signal to the radiographic image detector 5, the display unit 32 functions as notifying means for displaying a message to notify the operator of the result. On the display unit 32, the states of the respective units of the radiographic image detector 5 may always be displayed, or a message to notify that some abnormality has occurred in the unit(s) may be displayed only when abnormality has occurred.

The communication unit 33 communicates various types of information with the radiographic image detector 5 through the base station 4 by a wireless communication system such as a wireless LAN.

A signal inputted from the input operation unit 31, a signal received from the outside through the communication unit 33 and the like are sent to the control unit 29. The control unit 29 acquires a radiographic image such as a thumbnail image desired by a doctor and the like by, for example, performing predetermined image processing based on the radiographic image information detected by the radiographic image detector 5. Further, the control unit 29 allows the above-described display unit 32 to display the radiographic image such as the thumbnail image, various types of information inputted from the input unit, and the like.

Next, description will be made of a function of the radiographic imaging system 1 applying the radiographic image detector 5 according to this embodiment.

First, to perform imaging, the radiographic image detector 5 is used being detached from the cradle 23 and not connected to any external device. When it has been detected by the connection detecting unit 24 that the radiographic image detector 5 is detached from the cradle 23 and thus the connections between the connection terminals of the cradle 23 and the connection terminal 40 for charging and the connection terminal 41 for communication are released, the control unit 27 controls the remaining power detecting unit 42, wireless communication check unit 44 and memory check unit 19 to perform the state checks for the respective units of the radiographic image detector 5, the state checks including detection of amount remained in the internal power supply 20, communication check for the wireless communication unit 22 and the memory check for the image storing unit 18.

Then, when the control unit 27 has detected that the amount of power remained in the internal power supply 20 is the predetermined amount or more enough to allow imaging, that the wireless communication unit 22 can operate normally, and that the image storing unit 18 also has the memory capacity sufficient for storing the image information and can operate normally, the control unit 27 allows the internal power supply 20 to supply power to the respective units so that the radiographic image detector 5 can turn to an operation state capable of performing the imaging.

Here, the control unit 27 may control the indicator 25 to display that imaging is possible. Moreover, the control unit 27 may output the message that imaging is possible to the console 6 through the wireless communication unit 22. In this case, based on the signal inputted to the communication unit 33, the control unit 29 of the console 6 controls the display unit 32 to display that imaging is possible.

In contrast, when the amount of power remained in the internal power supply 20 is less than the predetermined amount, or when either the wireless communication unit 22 or the image storing unit 18 is in the state incapable of operating normally, the control unit 27 controls the indicator 25 to display that the radiographic image detector 5 is in a state unsuitable for imaging, and outputs a message that the radiographic image detector 5 is in the state unsuitable for imaging to the console 6 through the wireless communication unit 22. Here, based on the signal inputted to the communication unit 33, the control unit 29 of the console 6 controls the display unit 32 to display that the radiographic image detector 5 is in the state unsuitable for imaging. Note that the contents to be displayed on the indicator 25 and the contents to be transmitted to the console 6 are not limited to the above. For example, the indicator 25 may display information on what is making the radiographic image detector 5 unsuitable for imaging, such as the amount of power remained in the internal power supply 20, the state of the wireless communication unit 22 or image storing unit 18, and the like, and the information may be transmitted to the console 6.

When the reason why the radiographic image detector 5 is unsuitable for imaging is that the amount of power remained in the internal power supply 20 is less than the predetermined amount, the operator attaches the radiographic image detector 5 onto the cradle 23, and charges the internal power supply 20 of the radiographic image detector 5.

When the radiographic image detector 5 is attached onto the cradle 23, and the connection terminal 40 for charging and the connection terminal 41 for communication are connected to the connection terminals of the cradle 23, power is supplied from an external power supply (not shown) through the connection terminal 40 for charging, and the internal power supply 20 of the radiographic image detector 5 is charged. When it has been detected by the connection detecting unit 24 that the connection terminal 40 for charging and the connection terminal 41 for communication are connected to the connection terminals of the cradle 23, the control unit 27 controls the wired communication check unit 43 to perform the communication check for the wired communication unit 21. When it has been determined as a result of the state check that the wired communication unit 21 operates normally, the control unit 27 may further control the wireless communication check unit 44 to perform the communication check for the wireless communication unit 22. When either the wired communication unit 21 or the wireless communication unit 22 operates normally, the control unit 27 allows the image information and the like to be transmitted to an external device such as the console 6 from the normally operating unit between the wired communication unit 21 and the wireless communication unit 22. When both of the wired communication unit 21 and the wireless communication unit 22 operate normally, the control unit 27 allows the image information and the like to be transmitted to the external device through either one thereof.

When either the wired communication unit 21 or the wireless communication unit 22 is in a state of not operating normally, the control unit 27 allows the indicator 25 to display a message to indicate the above state, and transmits a signal indicating the state to the console 6. Upon receiving the signal concerning the state of the wired communication unit 21 or the wireless communication unit 22 from the radiographic image detector 5, the control unit 29 of the console 6 performs display as appropriate on the display unit 32 based on the received signal.

When the radiographic image detector 5 turns to an operation state capable of performing imaging, the control unit 27 performs initialization such as resetting the stored image information and idle reading to be ready for the next imaging. Then, when imaging is started and the irradiation if finished, the pulses are sent to the respective photoelectric conversion elements by the scan drive circuit 16 to scan and drive the respective photoelectric conversion elements. The electric energy stored in the respective photoelectric conversion elements is read by the signal reading circuit 17, and thus an image signal is acquired. The acquired image signal is stored in the image storing unit 18, and then transferred to the console 6 or the like as appropriate.

Note that, when the image signal is transferred with the radiographic image detector 5 being connected to the cradle 23, and when it has been detected by the connection detecting unit 24 that the connections of the connection terminal 40 for charging and the connection terminal 41 for communication to the connection terminals of the cradle 23 are released during the transfer of the image signal, it is recommended that the control unit 27 perform a check as to whether the image signal has been transferred normally, a memory check for the image storing unit 18 through the memory check unit 19, and the like, during the image transfer or after the image transfer.

Thus, according to this embodiment, when the connection of the radiographic image detector 5 to the cradle 23 is released, the amount of power remained in the internal power supply 20 and the states of the wireless communication unit 22 and image storing unit 18 are checked by the state checking means. There is a high possibility that the radiographic image detector 5 used without being connected to an external device at the time of imaging is used for imaging immediately after disconnected from the cradle 23. Therefore, the state checks for the respective units are performed at the time when the radiographic image detector 5 is disconnected from the cradle 23, and, prior to imaging, whether the respective units of the radiographic image detector 5 are in the state suitable for the imaging can be checked. In this way, an imaging failure owing to a shortage of the power and storage and transfer failures of an obtained image are prevented, and the frequency of performing re-imaging is suppressed. It is thus possible to prevent the patient from unnecessary exposure.

Moreover, when the amount of power remained in the internal power supply 20 is less than the predetermined amount, when the wired communication unit 21 and the wireless communication unit 22 are in the state incapable of transmitting and receiving information normally, when the memory capacity of the image storing unit 18 is insufficient, and so on, normal image information cannot be obtained even if imaging is performed, and the image cannot be stored or transferred to be wasted even if the image has been obtained. Therefore, it is necessary to perform re-imaging, and so on. Here, in this embodiment, the messages to indicate such cases are displayed on the indicator 25 and the display unit 32 of the console 6, and the operator is thus notified of the above. Therefore, imaging can be prevented from being erroneously performed in the states where normal image information cannot be obtained and where the image cannot be stored or transferred. In this way, it is possible to prevent unnecessary exposure.

Moreover, at the time of imaging, the radiographic image detector 5 is used without being connected to an external device. Accordingly, in comparison with the radiographic image detector 5 used in wired connection at the time of imaging, a degree of freedom in imaging operation can be improved, and operability of the radiographic image detector 5 according to this embodiment can be improved as a whole. Moreover, the radiographic image detector 5 includes the wired communication unit 21 and the wireless communication unit 22. Accordingly, it is possible to transmit and receive information such as an image through any of the wired and wireless systems, and thus the radiographic image detector 5 can be freely and suitably used in accordance with the imaging place and the like.

In this embodiment, the remaining power detecting unit 42, communication check units and memory check unit 19 are provided as the state checking means and are allowed to perform the state checks for the respective drive units. However, it is also possible to allow the above units to perform various state checks for drive units other than the above. In this case, one state check means may be allowed to perform plural state checks.

Specifically, the state checks include a reading state check for checking whether an image can be read normally by the signal reading circuit 17, and the like. Moreover, state checks for checking whether the photodiode 152 and the TFT 153 function normally may also be performed. The determination data necessary for the respective determinations of these state checks only need to be stored in the ROM and the like of the control unit 28 in the radiographic image detector 5.

Moreover, in this embodiment, the indicator 25 is provided as the notifying means of the radiographic image detector 5, the display unit 32 is provided as the notifying means of the console 6. When it has been determined the respective units of the radiographic image detector 5 are not in the normal state suitable for imaging, the message to indicate the above state is displayed on the indicator 25 and the display unit 32. However, the notifying means is not limited thereto. For example, an audio output unit may be provided as the notifying means, and an alarm sound or the like may be provided from the audio output unit, to notify the operator of the message. Moreover, only one of the indicator 25 and the display unit 32 of the console 6 may be provided as the notifying means.

Further, in this embodiment, when it has been determined that the states of the respective units are not in the normal state suitable for imaging, the indicator 25 or the display unit 32 of the console 6 generates a notice to indicate the above state. However, when the respective units are not in the normal state suitable for imaging, for example, the following control may further be performed. That is, a signal to indicate the state of the radiographic image detector 5 is transmitted from the console 6 to the radiographing operation device 3 or the radiographic imaging device 10, and an exposure button is locked so that the radiation cannot be emitted from the radiation source 12 of the radiographic imaging device 10, and soon. Moreover, when the control unit 27 has determined that it is impossible for the respective units to perform an operation normally, power supply from the internal power supply 20 may be controlled so that the radiographic image detector 5 cannot be capable of performing at least the imaging.

Moreover, when some abnormality has been found in the radiographic image detector 5, the control unit 27 may allow the radiographic image detector 5 to be restarted.

Further, in this embodiment, the radiographic image detector 5 is attached onto the cradle 23 as the connection means, and thus the connection terminal 40 for charging and the connection terminal 41 for communication in the radiographic image detector 5 are connected to the connection terminals of the cradle 23. In this way, the charging or the communication with an external device is performed. However, the connection means is not limited to the cradle 23. For example, a cable and the like may be connected to the connection terminal 40 for charging and the connection terminal 41 for communication in the radiographic image detector 5, and thus the charging or the communication with the external device may be performed.

Moreover, in this embodiment, the radiographic image detector 5 is attached to and detached from the cradle 23, and thus both of the connection terminal 40 for charging and the connection terminal 41 for communication are connected to and disconnected from the connection terminals of the cradle 23. However, different cables may be connected individually to the connection terminal 40 for charging and the connection terminal 41 for communication, and the connection detecting unit may detect connection to the external device or disconnection from the connection terminals.

Moreover, in this embodiment, the radiographic image detector 5 includes both of the connection terminal 40 for charging and the connection terminal 41 for communication; and however, the radiographic image detector 5 may include only one of the terminals.

Moreover, in this embodiment, the connection terminals 40 for charging and the connection terminal 41 for communication are provided separately from each other, and are connected individually to the corresponding connection terminals provided in the cradle 23 serving as both of the connection means for charging and the connection means for communication. However, one connection terminal serving as both of the connection terminal 40 for charging and the connection terminal 41 for communication may be provided in the casing 14, and this connection terminal and the connection terminal of the cradle may be connected to each other, to allow the radiographic image detector to be charged and perform communication with an external device.

Moreover, in this embodiment, the radiographic imaging device 10 is operated by the radiographing operation device 3; however, the radiographic imaging device 10 may be operated by the console 6 or the like. In this case, it is not necessary to provide the radiographing operation device 3, and thus the system configuration can be simplified.

Moreover, in this embodiment, the control unit 27 controls, besides the internal power supply 20, all of the drive units constituting the radiographic image detector 5, which include the scan drive circuit 16, signal reading circuit 17, wired communication unit 21, wireless communication unit 22 and the like. However, the respective drive units of the radiographic image detector 5, which include the internal power supply 20 scan drive circuit 16, signal reading circuit 17, wired communication unit 21, wireless communication unit 22 and the like, may be controlled individually by control units separate from one another.

The entire disclosure of Japanese Patent Application No. Tokugan 2005-068111 filed on Mar. 10, 2005, including specification, claims, drawings and summary are incorporated herein by reference in its entirety.

What is claimed is:

1. A radiographic image detector to detect radiation applied thereto and obtain radiographic image information, comprising:
   an internal power supply to supply power to drive units at least at a time of imaging;
   a communication unit to perform communication with an external device;
   a connection terminal connectable to a connection unit which performs at least one of charging of the internal power supply and the communication with the external device;
   a storing unit to store at least one of an image and information;
   a connection detecting unit to detect whether the connection terminal is connected to the connection unit;
   a state checking unit to check a state of each unit; and
   a control unit to control the state checking unit such that the state checking unit checks the state of each unit when the connection detecting unit has detected that the connection unit is connected to the connection terminal or disconnected therefrom.

2. The radiographic image detector of claim 1, wherein the state checking unit includes at least any one of a remaining power detecting unit to perform a check for an amount of power remained in the internal power supply, a communication check unit to perform a communication check for the communication unit, and a memory check unit to perform a memory check for the storing unit.

3. The radiographic image detector of claim 2, wherein the communication unit includes a wired communication unit to perform wired communication with the external device and a wireless communication unit to perform wireless communication with the external device, and the communication check unit performs a communication check for at least one of the wired communication unit and the wireless communication unit.

4. The radiographic image detector of claim 1, wherein the connection terminal is any one of a charging connection terminal connectable to a charging connection unit to charge the internal power supply and a communication connection terminal connectable to a communication connection unit to perform communication with the external device, and the control unit controls the state checking unit to perform the state check for each unit in at least one of cases where the connection detecting unit has detected that the charging connection terminal is connected to or disconnected from the charging connection unit and where the connection detecting unit has detected that the communication connection terminal is connected to or disconnected from the communication connection unit.

5. The radiographic image detector of claim 2, wherein the connection terminal is any one of a charging connection terminal connectable to a charging connection unit to charge the internal power supply and a communication connection terminal connectable to a communication connection unit to perform communication with the external device, and the control unit controls the state checking unit to perform the state check for each unit in at least one of cases where the connection detecting unit has detected that the charging connection terminal is connected to or disconnected from the charging connection unit and where the connection detecting unit has detected that the communication connection terminal is connected to or disconnected from the communication connection unit.

6. The radiographic image detector of claim 3, wherein the connection terminal is any one of a charging connection terminal connectable to a charging connection unit to charge the internal power supply and a communication connection terminal connectable to a communication connection unit to perform communication with the external device, and the control unit controls the state checking unit to perform the state check for each unit in at least one of cases where the connection detecting unit has detected that the charging connection terminal is connected to or disconnected from the charging connection unit and where the connection detecting unit has detected that the communication connection terminal is connected to or disconnected from the communication connection unit.

7. The radiographic image detector of claim 2, wherein the connection terminal is a charging connection terminal connectable to a charging connection unit to charge the internal power supply, and the control unit controls the state checking unit to perform at least any one of the check for the amount of power remained in the internal power supply, the communication check for the communication unit and the memory check for the storing unit when the connection detecting unit has detected that the charging connection terminal is disconnected from the charging connection unit, and controls the state checking unit to perform the communication check for the communication unit when the connection detecting unit has detected that the charging connection terminal is connected to the charging connection unit.

8. The radiographic image detector of claim 3, wherein the connection terminal is a charging connection terminal connectable to a charging connection unit to charge the internal power supply, and the control unit controls the state checking unit to perform at least any one of the check for the amount of power remained in the internal power supply, the communication check for the communication unit and the memory check for the storing unit when the connection detecting unit has detected that the charging connection terminal is disconnected from the charging connection unit, and controls the state checking unit to perform the communication check for the communication unit when the connection detecting unit has detected that the charging connection terminal is connected to the charging connection unit.

9. The radiographic image detector of claim 3, wherein the connection terminal is a communication connection terminal connectable to a communication connection unit to perform communication with the external device, and the control unit controls the state checking unit to perform at least any one of the communication check for the wireless communication unit, the check for the amount of power remained in the internal power supply, and the memory check for the storing unit when the connection detecting unit has detected that the communication connection terminal is disconnected from the communication connection unit, and controls the state checking unit to perform the communication check for the communication unit when the connection detecting unit has detected that the communication connection terminal is connected to the communication connection unit.

10. The radiographic image detector of claim 1, further comprising a notifying unit to notify that the state checking unit has detected that a state of each unit is not normal.

11. The radiographic image detector of claim 1, wherein the radiographic image detector is a cassette-type flat panel detector to detect radiation applied thereto, convert the radiation into an electric signal, store the electric signal, and read the stored electric signal, to acquire the radiographic image information.

12. A radiographic imaging system comprising: the radiographic image detector of claim 1; and a console to operate the radiographic image detector.

13. The radiographic imaging system of claim 12, wherein the console comprises:
    a communication unit to perform communication with the radiographic image detector; and
    a notifying unit to notify that the communication unit has received a signal indicating that the state checking unit of the radiographic image detector has detected that each unit is not normal.

\* \* \* \* \*